(12) United States Patent
Spitler et al.

(10) Patent No.: US 6,812,035 B1
(45) Date of Patent: Nov. 2, 2004

(54) DYE DESORTION MOLECULAR INDICATOR

(75) Inventors: Mark T. Spitler, Concord, MA (US); Louis S. Stuhl, Bedford, MA (US)

(73) Assignee: Chemmotif, Inc., Concord, MA (US)

( * ) Notice: Subject to any disclaimer, the term of this patent is extended or adjusted under 35 U.S.C. 154(b) by 0 days.

(21) Appl. No.: 09/350,466

(22) Filed: Jul. 9, 1999

Related U.S. Application Data (60) Provisional application No. 60/092,394, filed on Jul. 10, 1998.

(51) Int. Cl.[7] ............................................. G01N 21/77
(52) U.S. Cl. ........................... 436/169; 422/56; 422/57; 422/82.05; 422/58; 436/170
(58) Field of Search ................................ 436/169, 170; 422/58, 56, 57, 82.05

(56) References Cited

U.S. PATENT DOCUMENTS

| | | | |
|---|---|---|---|
| 3,635,679 A | 1/1972 | Bloch et al. ............... 23/230 R |
| 3,992,158 A | 11/1976 | Przybylowicz et al. . | 23/253 TP |
| 4,042,335 A | 8/1977 | Clement .................. | 23/253 TP |
| 4,144,306 A | 3/1979 | Figueras ..................... | 422/56 |
| 4,166,093 A * | 8/1979 | Smith-Lewis et al. ........ | 422/56 |
| 4,212,153 A * | 7/1980 | Kydonieus et al. ........... | 368/62 |
| 4,255,384 A | 3/1981 | Kitajima et al. .............. | 422/57 |
| 4,256,694 A | 3/1981 | McAllister et al. ........... | 422/58 |
| 4,258,001 A | 3/1981 | Pierce et al. .................. | 422/56 |
| 4,303,408 A | 12/1981 | Kim et al. ................. | 23/230 B |
| 4,356,149 A | 10/1982 | Kitajima et al. .............. | 422/56 |
| 4,421,719 A | 12/1983 | Burleigh ...................... | 422/57 |
| 4,594,225 A | 6/1986 | Arai et al. .................... | 422/56 |
| 4,597,942 A | 7/1986 | Meathrel ...................... | 422/57 |
| 4,789,525 A | 12/1988 | Warren, III et al. .......... | 422/56 |
| 4,946,705 A | 8/1990 | Manning et al. ............... | 427/2 |
| 4,966,784 A | 10/1990 | Tanaka et al. ................. | 427/2 |
| 5,114,676 A | 5/1992 | Leiner et al. ............ | 422/82.06 |
| 5,122,451 A * | 6/1992 | Tanaka et al. ................ | 435/74 |
| 5,147,806 A | 9/1992 | Kamin et al. ............... | 436/149 |
| 5,175,110 A | 12/1992 | Bradshaw et al. ............ | 436/77 |
| 5,186,894 A | 2/1993 | Katsuyama ................... | 422/56 |
| 5,200,321 A | 4/1993 | Kidwell ....................... | 435/7.9 |
| 5,290,704 A | 3/1994 | Chang ........................ | 436/128 |
| 5,294,402 A | 3/1994 | Schrepp et al. ............... | 422/57 |
| 5,340,748 A | 8/1994 | Baugher et al. ............. | 436/518 |
| 5,354,652 A | 10/1994 | Silbergeld ....................... | 435/4 |
| 5,409,814 A | 4/1995 | Berry et al. ................... | 435/22 |
| 5,413,915 A | 5/1995 | Case et al. .................... | 435/25 |
| 5,418,136 A | 5/1995 | Miller et al. .................... | 435/5 |
| 5,552,272 A | 9/1996 | Bogart .......................... | 435/6 |
| 5,822,280 A * | 10/1998 | Haas ........................... | 368/327 |
| 5,858,307 A | 1/1999 | Neihof ........................ | 422/61 |
| 5,891,649 A | 4/1999 | Kidwell et al. .............. | 435/7.9 |
| 6,214,623 B1 * | 4/2001 | Simons et al. ................. | 436/2 |

* cited by examiner

*Primary Examiner*—Jill Warden
*Assistant Examiner*—LaToya I. Cross
(74) *Attorney, Agent, or Firm*—Weingarten Schurgin, Gagnebin & Lebovici LLP

(57) ABSTRACT

A method of broad screen detection, competitive dye desorption from a solid adsorbent, is described for quantifying the presence of a molecule or target analyte in the vapor phase, in solution, or eluted from a solid. In the function of an analytical element for implementing the competitive dye desorption method of the invention, dye or dye-precursor molecules adsorbed on the surface of an adsorbent are caused to desorb through the adsorption of the target analyte on the adsorbent. The desorbed dye or precursor is made detectable through sequestering of a radiation detectable species in the device of the invention. Such detection may occur, e.g., through absorption or emission of radiation in regions of the spectrum extending from the ultra-violet through the visible and into the infra-red regions. In one aspect of the invention, these processes occur within a multi-layer analytical element, in which the functions of the device may be executed by different layers.

22 Claims, 3 Drawing Sheets

DYE DESORPTION MOLECULAR INDICATOR

CROSS REFERENCE TO RELATED APPLICATIONS

This application claims the priority of U.S. Provisional Patent Application No. 60/092,394 filed Jul. 10, 1998 entitled DYE DESORPTION RESIDUAL LIFE INDICATOR, the whole of which is hereby incorporated by reference herein.

STATEMENT REGARDING FEDERALLY SPONSORED RESEARCH OR DEVELOPMENT

The experiments leading to this invention were supported in part by the SBIR program of the United States Army, Grant No. DAAN02-98-P-8052. Therefore, the U.S. Government has certain rights in this invention.

BACKGROUND OF THE INVENTION

New devices for the broad screen detection of contaminants or pollutants in a solution or in a gas phase are widely desired for use in evaluation of, e.g., water supplies, hazardous waste sites, and work place environments. Many present forms of such, analyses involve the use of expensive instrumentation. For example, analysis of water supplies for total chlorine content, chlorocarbons, or pesticide residues requires the use of high performance liquid chromatography, mass spectroscopy or UV-VIS spectroscopy. At hazardous waste sites, ground water and surface water are analyzed in a similar fashion. Detection of volatile organic hydrocarbons (VOCS) in soils, on the other hand, involves the head space analysis of the vapor above the soil samples through the use of gas chromatography. Detection of pesticide residues involves mass spectroscopic analysis of chromatographically separated samples.

It is known that metal ions can be detected through a color change brought about by the reaction of the ions with a ligand or chelating agent. Metals can inhibit the activity of enzymes, an aspect that can be used to quantify their concentration. They can also stimulate the activity of enzymes through the release of substrates for the enzyme; this heightened activity can also be: quantified. Such methods are known to be applicable to molecules and ions other than metals.

Immunoassay methods are known to be sensitive in their response to target analytes. Biologically active organisms such as *Helicobacter pylori* and Streptococcus species can be detected. The antibody-antigen interaction is utilized to produce a detectable event upon exposure of the device to the target analyte. Fluorescent species can be released that can be detected instrumentally; electrochemical means can be used to amplify the signal. Interference patterns can be induced by such reactions through a change in film thickness, which can be quantified.

Many of these analytical methods have been assembled in analytical devices with a multilayer construction that separates an analyte detection from the readout function. There are several strategies in the art of multilayer analytical elements which have been devised for detection of specific molecules, ions, contaminants, or pollutants.

It is well known that metal ions in solution such as ferrous or ferric ions, calcium, lead or zinc can be detected through such a multilayer element. The target analyte reacts with a reagent within one of the layers of the device to produce a colored change that can be quantified calorimetrically. The concentration of the colored species can be assessed visually through a comparison with standards or measured with an instrument in either a transmissive or reflective mode. In the reflective mode, the detection layer resides upon a transparent polymer base but in front of a reflective pigment layer.

The detection of metal ions can be accomplished through a number of variations on this procedure. Ferrous ions can be chelated by reagents within a multilayer element that provides a buffered environment for its migration to a detection layer. The chelating agent may be resident in this detection layer. Similar arrangements are known for the detection of $Ca^{++}$ in aqueous solutions. Interferences may be removed by the presence of additional reagents such as the addition of calcium chelating reagents to a multilayer analytical element designated for detection of magnesium.

Multilayer analytical elements have been devised for the assay of complex fluids, such as blood. Such elements can be composed to detect glucose, alcohol, cholesterol, or proteins. In the analysis of such complex fluids, separation layers impregnated with separation agents are used to isolate the target analyte from the other components of the blood. Such analyses of biological fluids often rely upon enzymes to produce the color change for detection of the target analyte. The analyte can interfere with a color-producing reaction by the enzyme, or it can induce the enzyme to produce a colored species.

Immunoassay methods make use of antibody/antigen binding to effect specific sensitivity in multilayer analytical elements. Enzymes specific to an analyte are synthesized and coated within such a device to bind the target molecule and induce a measurable readout signal through the release of a molecule which can migrate to a registration layer. Usually this is a fluorescent assay that requires a photodetector for interpretation.

BRIEF SUMMARY OF THE INVENTION

In the present invention, a novel means of broad screen detection is described for the presence of target analytes in the vapor phase, in solution, or eluted from a solid. In the invention, the novel application of competitive dye desorption from a solid adsorbent is employed as a method of quantifying the presence of the molecule or target analyte. In the function of an analytical element for implementing the competitive dye desorption method of the invention, dye or dye-precursor molecules adsorbed on the surface of an adsorbent are caused to desorb through the adsorption of the target analyte on the adsorbent. The desorbed dye or precursor is made detectable through sequestering of a radiation detectable species in the device of the invention. Such detection may occur, e.g., through absorption or emission of radiation in regions of the spectrum extending from the ultra-violet through the visible and into the infra-red regions.

In one aspect of the invention, these processes occur within a multi-layer analytical element, in which the functions of the device may be executed by different layers. Such an integral, multi-layer element will include an analyte acquisition layer, which contains the substrate for dye desorption from which dye is desorbed in response to the presence of the analyte within the layer, and an underlayer in which the desorbed dye is sequestered in a detectable manner.

BRIEF DESCRIPTION OF THE SEVERAL VIEWS OF THE DRAWING

Other features and advantages of the invention will be apparent from the following description of the preferred embodiments thereof and from the claims, taken in conjunction with the accompanying drawings, in which:

DETAILED DESCRIPTION OF THE INVENTION

In the devices of the invention, a relatively loosely adsorbable dye or dye precursor is adsorbed onto an adsorbent to serve as the analyte detector. The adsorbent can be coated on a substrate, e.g., as a film or a coating on any surface in a binder medium that will permit adsorbate adsorption, desorption, and diffusion and used, e.g., in a badge for contaminant exposure detection. Exposure to analyte, e.g., in the air, displaces the dye or its precursor and the dye or its precursor is detected. In the case of a precursor, materials can be provided elsewhere in the analytical element to react with it and produce a radiation detectable species. As used in this application, the term "dye" should be taken to include the use in this invention of molecules that are not directly detectable but can be converted to detectable form within the analytical element by chemical or physical processes. As illustrated in FIGS. 1a–1d, the displaced or newly formed dye then diffuses to a receiving registration layer, for example a dye mordanting layer. This layer is coated below the adsorbent layer and on a transparent base, and dye will accumulate there.

Furthermore, the term "dye" is intended to include an embodiment in which the displaceable material adsorbed on the adsorbent is a catalyst for the formation of a radiation detectable species, e.g., for a color-forming reaction in which the color-forming precursor reagents are incorporated into other layers, for example, directly into the mordant. Competitive displacement of the catalyst by analyte adsorption enables the us catalyst to come into contact with, e.g., the color precursors to produce color in the mordant. Because the system is catalytic, the amount of dye formed can be many times the amount of analyte adsorbed, depending on the catalyst turnover number and the amount of precursor reagents present.

Diffusion into the registration layer is facilitated by including a polar, high boiling plasticizer/solvent in at least one of the layers of the analytical element to create a liquid-like environment. Plasticizers are high boiling solvents that permit substances to migrate within the coatings. The dye on the adsorbent and in the mordant are at equilibrium with dye solvated by the plasticizer which permeates the entire structure.

The conceptual basis of the invention is revealed through an examination of model isotherms such as a Langmuir-type isotherm, for dye adsorption in the adsorbent and mordant layers. The selection of the adsorbent and mordant composition is made so that the free energy of binding of the dye to the two differs by at least an order of magnitude. This difference results in two distinctly different isotherms, as depicted in FIG. 4.

Figure 4:
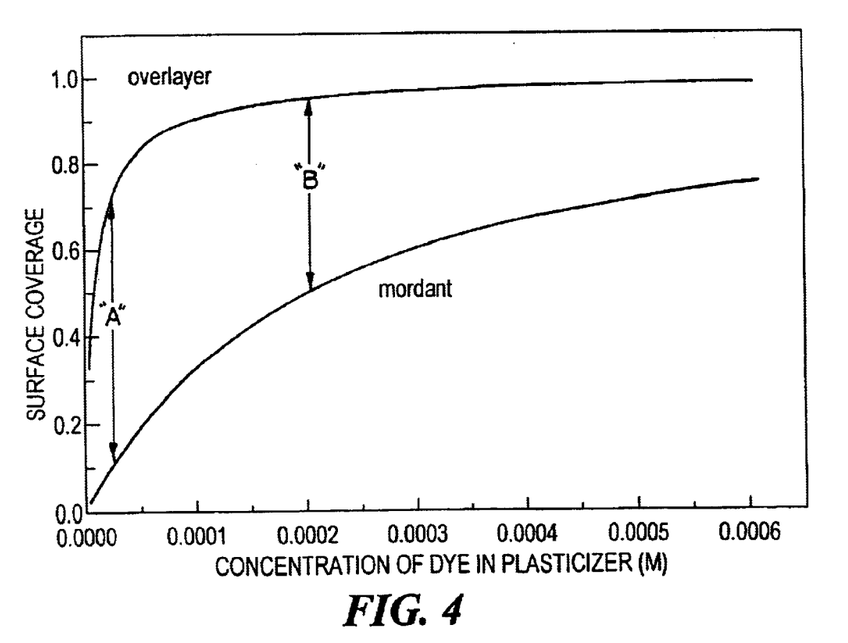
FIG. 4 shows a desirable relationship between the strengths of adsorption of a given dye onto an adsorbent and a mordant material.

Before exposure to an analyte, the system is poised at point "A" on the isotherms, as shown in FIG. 4, where the surface coverage of the adsorbent is maximized and very little dye is present in the mordant. As dye is displaced from the adsorbent by the analyte, the amount of dye in the plasticizer will increase to some point "B", which correlates with a much higher dye concentration in the mordant.

The sensitivity of the system is a strong function of the absolute amount of dye in the carbon overlayer. The practical range of optical density for the dyes in the mordant layers is 0–2 OD (OD=optical density), for that is the range over which the human eye can distinguish such intensity changes. This corresponds to a dye coverage in the mordant of up to $2 \times 10^{-8}$ moles/cm$^2$. For example, a milligram of activated carbon can adsorb $2 \times 10^{-7}$ moles of dye, so there is a wide range of sensitivity control available through the carbon coating coverage.

However favorable the thermodynamics of the system, the kinetics of the system must be adequate as well. The dye must have a low but non-zero rate of desorption from adsorbent into the plasticizer as well as a reasonable rate of diffusion, $1 \times 10^{-7}$ cm$^2$/s, as is found for molecules in gelatin within the plasticizer to the mordant, so that the image will develop within a reasonable time following exposure.

Among the many factors determining the strength of an adsorbent/adsorbate interaction, molecular size, weight, and polarity and molecular polarizability are usually the most important. Molecular size and weight affect an adsorbate's volatility and surface area available for binding to an adsorbent. Polarity determines the coulombic aspects of adsorption.

Molecular polarity is composed of several components, but it can be visualized as the extent to which electronic charge is non-uniformly distributed in a molecule. For example, for activated carbon or related adsorbents, the most strongly bound analytes will generally be materials of low polarity, high molecular weight, or both. The strength of adsorption of normal alkanes is proportional to the number of carbons in the molecule. In contrast, for polar adsorbents such as silica, the most strongly bound adsorbents will generally be materials of high polarity, and the effect of molecular weight will be minimal.

The plasticizer/solvent also will play a role in the energetics of adsorbent/adsorbate interactions. Adsorption will be strongest when the solubility of the adsorbate is lowest. Therefore, the choice of plasticizer/solvent can also influence device response and selectivity. As a result of the wide range of adsorbents and adsorbates that can be combined, the invention has very wide application. Embodiments can be developed on the basis of analyte polarity, solubility in the plasticizer/solvent, or on specific interactions with the adsorbent. Selectivity for particular materials can be attained by altering dye molecular structures to control relative binding strength to the adsorbate. The dye, adsorbent, and plasticizer/solvent act as a group to establish the selectivity for different analytes. The choice of other embodiment components, particularly any binder used to hold the adsorbent, can also affect the selectivity. The invention can be implemented to provide sensitivity to either a broad range of analytes, or to very specific types of analytes, depending on the type of adsorbent-adsorbate interactions selected. Specific examples of adsorbent/adsorbate pairs are given in Table 1.

TABLE I

| Adsorbate/Adsorbent/Plasticizer | Response |
| --- | --- |
| Methylene Blue/*DARCO G-60 carbon/1,4-butanediol | arene > alkene ≧ alkane |
| Disperse Red 19/*MAXSORB carbon/propylene carbonate | cyclic alkene > arenes ≈ alkane |

*DARCO G-60 is activated carbon from American Norit Co., Inc.
MAXSORB is activated carbon from Kansai Coke and Chemical.

The invention is capable of being implemented so that a variety of incident radiation-detectable changes can provide the read-out method for a device incorporating this invention. Dye desorption can provide either a direct optical read-out for visual or instrumental assessment; systems can be constituted so that either the appearance of color or a change in color occurs. Other read-outs can include the appearance or disappearance of fluorescence or signaling at wavelengths outside the visual range. A system based on the disappearance of color can be constructed around the release of a colorless adsorbate that can bleach a dye already present in the registration layer. Especially if fluorescence is the detection method of choice, the binder of the adsorbent can serve as the registration or sequestering region, and the binder/adsorbent complex can be coated directly on a surface to enable analyte detection over an area.

In another example, the mordant and transparent base of the sensor are replaced by a transparent base on which is coated a conductive transparent oxide layer. This layer can be tin oxide or indium tin oxide (ITO) or any other transparent conductive material. Thus, the structure of the resulting device is base/ITO/titania(optional)/carbon. The dye desorbed from the adsorbent, e.g., carbon, by the incident analyte molecule can diffuse to adsorb onto the ITO. The presence of the adsorbed dye will make the ITO photoconductive at the wavelengths where the dye absorbs light. Thus, the resistance of the ITO layer will change under illumination, and if electrical contacts are made to the ITO, this change in resistance can be quantified electronically to provide an electronic readout correlated with the concentration of the target analyte. In such an application, the sensor element would be packaged as a cartridge that is inserted into a small electronic device constructed to measure its photoconductivity and, therefore, the extent of exposure to the target analyte.

Another useful embodiment of this invention is one in which varying levels of one or more dyes are coated in separate sections of the analytical element, so that color appears in different places on the viewing side as a function of the amount or types of analyte detected. It is also possible to adsorb two dyes with differing adsorption strengths onto the adsorbate, so that as the level of analyte exposure increases, the color observed both increases and shifts hue.

Figure 5:
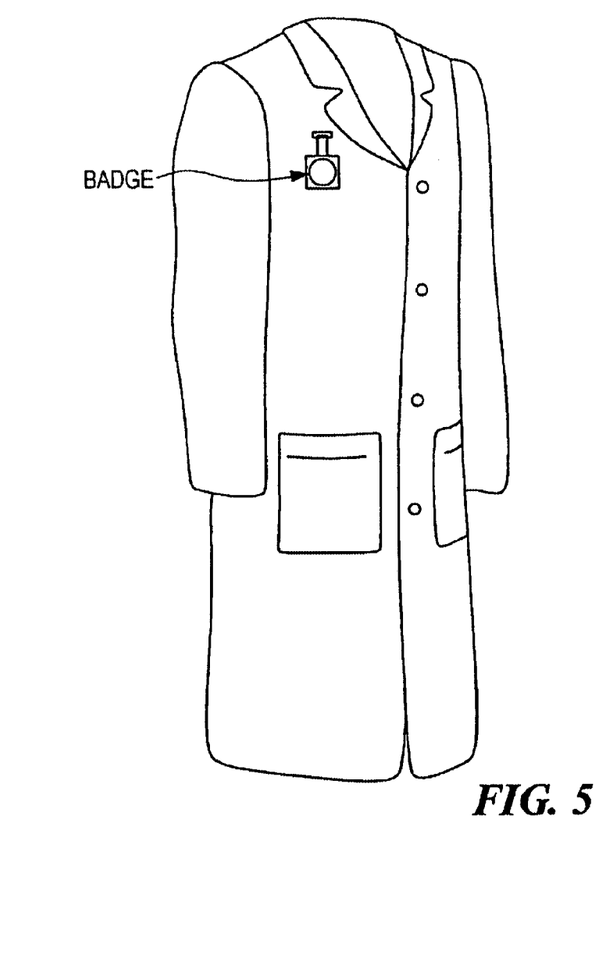
FIG. 5 shows an analyte detection badge incorporating the analytical detection element of the invention.

One way that an analytical device incorporating competitive desorption as a means of chemical detection can be assembled is to build the device as an integral, multilayered analytical element, which can be worn, e.g., as an analyte detection badge, as shown in FIG. 5. The construction of such analytical elements using other methods of analysis is well-documented in the prior art. Such elements are simple in structure, easily manufactured at reasonable cost, and adapted to carry out the analysis in a simple and effective manner.

Figure 6:
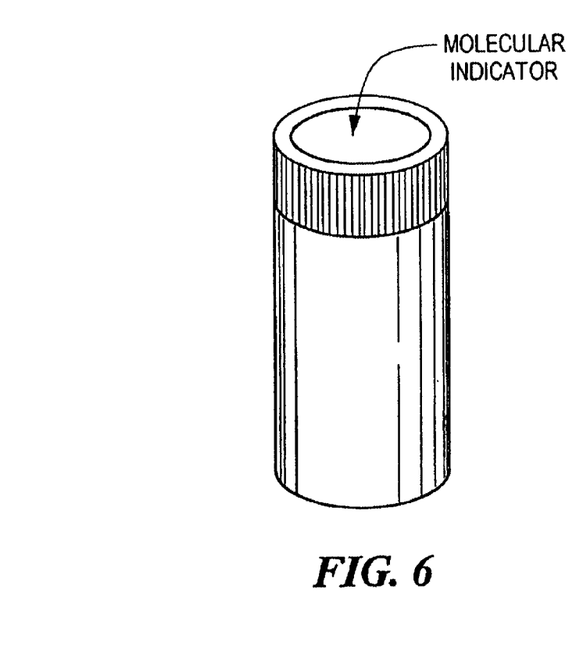
FIG. 6 shows an analyte detection container incorporating the analytical detection element of the invention.

In another implementation, a device according to the invention is used for measurement of molecules in vapor phase above liquids and solid samples. Referring to FIG. 6, such a device consists, e.g., of a vial, jar or other container into which is placed a liquid or solid sample to be analyzed for the presence of volatile compounds, and of a cap with which the container is sealed. The analytical, or sensor, element is placed inside the closed vessel, either on the side of the jar or in the cap, in such a way that the readout is visible through the transparent walls of the vessel or through the transparent cap. When the sample is sealed within the container, the volatile components emanating from the sample are detected by the sensor element in the manner described above to induce a color readout visible from the outside of the vessel.

The analytical element can be in the form of sheets, short strips, continuous tapes or strips, or as small sections or chips that may or may not be mounted in aperture cards or other external mountings. In addition, the detection element can be provided in multiple small pieces, e.g., as confetti or in shredded form, that can be spread over an area to detect the presence of target analyte(s) within that area. Furthermore, although the preferred form of the invention is a multilayered element, the invention is not limited to this form. Rather, it is directed to any element using competitive displacement of dyes or radiant energy-detectable materials or precursors from adsorbents in a solid but molecularly permeable medium as a means for the detection and analysis of chemical substances. Radiant energy-detectable refers to a species that, through the formation or loss of color, fluorescence, or other characteristics, alters the radiant energy reflection or transmission characteristics of the analytical element.

The integral, multilayer analytical element is typically laminar in construction, so that when observed as a transverse cross-section, the layers are seen as superposed. This construction permits the desorbed species to diffuse from the outermost layers into one or more interior layers. In use, the element may simply be exposed to the air or other gases containing vapors to be analyzed. Alternatively, liquids may be applied directly to an appropriately designed element top surface, for example as described in U.S. Pat. No. 3,992,158 or many other designs known in the art.

In a preferred embodiment, the element includes a support, a layer overcoated or otherwise integrally formed on one side of the support and including at least one indicator substance, a layer providing a background for viewing the signal produced by the indicator substance, and a layer at or near the top of the layer stack that contains the adsorbent and competitively desorbable species, which is accessible by the analyte(s) to be detected.

The drawings further illustrate the invention. Each layer is shown coextensive with the adjacent layers. It will be appreciated that certain layers could extend beyond the active area of the element without altering the nature of the element.

Figure 1A:
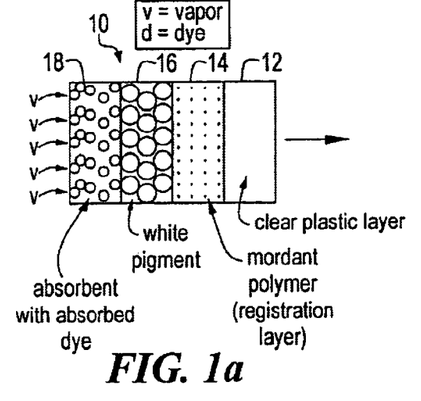
FIG. 1 is an illustration of the manner in which dye desorption off of an adsorbent can serve as a vapor detection mechanism.
Figure 1B:
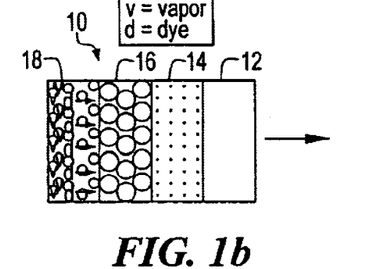
Figure 1C:
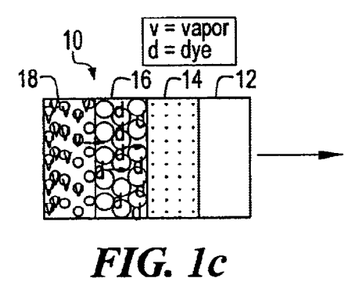
Figure 1D:
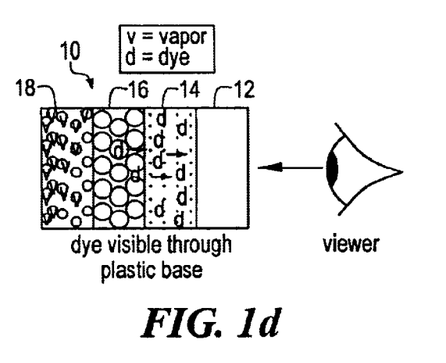

A working embodiment of an integral, multilayer analytical element needs to incorporate several functions: sample capture, competitive desorption, concentration of the released radiant energy-detectable materials and, if the adsorbent is colored or significantly opaque, provision of a background against which the radiant energy-detectable materials can be detected. In certain embodiments, it is possible to combine certain of these functions into single layers. For detection of vapor analytes, it is preferred to construct the element as a three layer structure atop a transparent base, readable by reflectance. Referring to FIGS. 1a–1d and to FIG. 2, four components can be present in analytical element (10), in order of distance from the base:

the clear plastic base (12) itself, the concentrating layer (14) such as a dye mordanting layer, a reflecting layer (16), e.g., a white pigment, that also is sufficiently opaque to appear white under a dark adsorbent, and the adsorbent/indicator layer (18), which for vapor detection serves also as the sample capture layer. As illustrated in FIG. 1a, analytes in the vapor phase (v) diffuse into adsorbent/indicator layer (18), where, as shown in FIG. 1b, the analytes to be detected competitively displace the displaceable dye or dye precursor adsorbed onto the adsorbent. FIGS. 1c and 1d show displaced dye molecules diffusing through reflecting layer (16) and collecting in concentrating layer (14), where they are detectable through clear plastic base (12).

Figure 3:
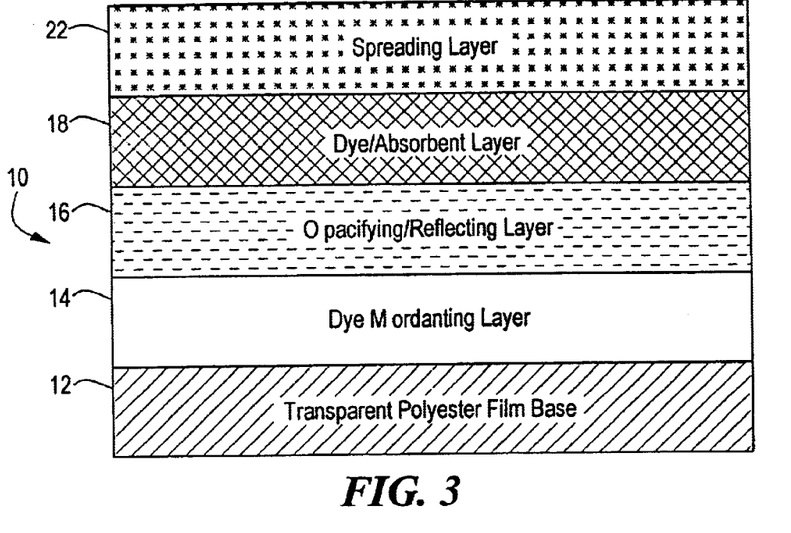

If an analytical element (20) is intended to be used with liquid samples, an appropriately designed top surface (22), as shown in FIG. 3, may be used to receive the liquid directly. The sample fluid can itself serve to swell the layers and transport the desorbed radiant energy-detectable species or precursor to the concentrating layer for read-out. However, it may be desirable either to increase swell or transport rates or to minimize sample size requirements to incorporate a fluid into one or more of the layers. In the case of vapor phase samples, such fluid incorporation is mandatory. This fluid will in essence be a plasticizer for the polymer film-formers in the structure, as it must be compatible with the polymers, capable of swelling them but not of altering their mechanical integrity. It should have a sufficiently high boiling temperature so that it does not evaporate significantly during the use life of the element. This plasticizer must also be a solvent for the mobile species that will be or will lead to the detectable species. Thus, it will be referred to henceforth as the plasticizer/solvent. However, unless indicated otherwise, all references to plasticizer/solvent can also include, when relevant, the case of the sample fluid itself serving as the plasticizer/solvent.

Key to the design of a working system is the choice of film-forming binders and plasticizer/solvents. These are selected based on the relative polarities and hydrophilicities of the analyte(s), adsorbents, and indicating materials (dye or precursor). Thus, in the case of a nonpolar adsorbent such as activated carbon being used to detect relatively low polarity analytes, the dye or dye precursor could be chosen to be more polar so that the analyte could displace it from the carbon surface. This in turn would require a sufficiently polar plasticizer/solvent that the dye would be dissolved and be transported by it. This in turn would limit the choice of polymer binders to those that could dissolve significant amounts of plasticizer/solvent and be plasticized by it.

In the present case, a hydrophilic, high boiling organic solvent that is not so polar as to exclude the analyte of interest might be selected. Such solvents can include alcohols, diols and higher polyols, sulfoxides, amides, esters, carbonates, ketones, and the like. Any solvent that will achieve the above goals and be stable under coating, storage, and use conditions can be a candidate. The polymer (s) used as binders for the different layers must be selected for compatibility with the selected plasticizer/solvent. In the case of analytical elements constructed around water as coating solvent, water soluble or highly swellable polymers such as polyvinyl alcohol, gelatin, hydroxyalkylcellulose ethers, N-vinyl pyrrolidone polymers and copolymers, carrageenan and other natural polysaccharide gums, carboxymethylcellulose, polyacrylamide and its copolymers, and other film forming, hydrophilic polymers could be suitable.

Many of the same polymers would also be appropriate for use with diols and polyols, and more polar alcohols such as polyethylene glycol monoethers. For polar but non-hydrogen bond donor solvents such as amides or sulfoxide, water-insoluble polymers such as polyvinyl butyral, acrylate copolymers, polyvinyl acetate and copolymers, cellulose esters and ethers, copolymers of styrene with polar monomers such as maleic anhydride or N-vinyl pyrrolidone, and other polymers with the right solubility parameters for the solvent in question would be appropriate.

For the opposite polarity situation, in which the choice of a polar adsorbent like silica or alumina and a relatively nonpolar dye leads to the choice of a hydrophobic, less polar solvent, there is a wide range of possible commercially available solvents that could be paired with standard thermoplastic polymers. Examples of suitable solvents include dialkyl diesters such as those sold as the DBE series (DuPont), diesters of aryl compounds including those commonly used as plasticizers for, e.g., polyvinyl chloride, polyvinyl acetate, cellulose nitrate, and the like, such as diethyl phthalate, long chain esters such as isopropyl palmitate, phosphate esters like tributyl phosphate, liquid chloroparaffins, sulfonamides like N-ethyl-o,p-toluenesulfonamide, amides such as diethyl lauramide, ethoxylated or propoxylated phenols such as IGEPAL OD-410 (Rhodia), and many others. A specific example might be the combination of polystyrene with dimethyl sebacate.

It is not necessary that the same polymer binder(s) be used in each layer. Depending on the coating method used, it may actually be easier to vary the binders between layers to minimize interlayer mixing. The standard considerations around interlayer wetting and adhesion, and the effects of differential swelling and thermal response should be observed. Also, some layers will differ in binder(s) simply because a polymer is a functional element within the layer.

It may also De desirable to crosslink one or more layers to control swelling during overcoating. The choice of crosslinker will of course be dependent on the binder and drying conditions chosen. Alternatively, polymers that become insoluble on drying, for instance polyvinyl acetate lattices, or ones that become insoluble on heating such as ammonium salts of base-soluble but neutral water-insoluble polymers like CARBOSET 525 (BFGoodrich) or SCRIPSET 520 (Solutia), can provide swelling control either as primary binders or as additives.

Figure 2:
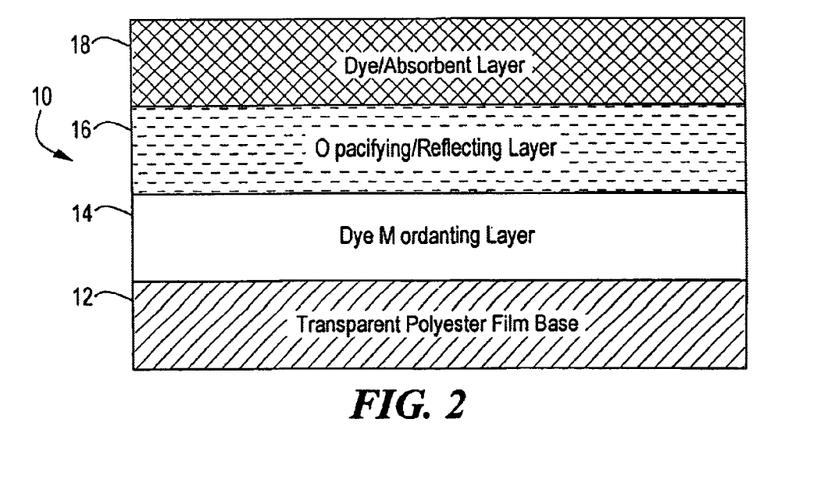
FIGS. 2 and 3 show enlarged sectional views of analytical elements incorporating the invention for the purpose of vapor and liquid analysis respectively.

A specific realization of the dye desorption concept for chemical analysis is a multilayer, integral analytical element. Such an element can be targeted to either vapor or liquid samples. The analytical read-out can be the appearance of a color, a change in color, the appearance or disappearance of fluorescence, or any other incident radiation-readable or otherwise detectable change in the appearance of a signaling layer. FIG. 2 represents a three layer, wet coated film that demonstrates this concept. The analyte is adsorbed on the side opposite the transparent base, and the signal is read through the transparent base. A discussion of the issues involved in the design of such a system follows.

The Base

In principle, any substrate that can receive the coated layer and that does not interfere with optical detection is suitable. Such substrates can include plastic films, paper, nonwoven sheets, metal foils and the like. For the preferred embodiment in which the signal is observed in a concentrating layer separated from the detecting layer by an opaque reflecting layer, the coating substrate must have some degree of transparency. This is most easily achieved by the use of plastic films. The thickness of these films can be any amount that is convenient and compatible with the coating apparatus used.

These films can be composed of materials such as polyethylene terephthalate, polybutylene terephthalate, polyethylene naphthalate, polylactic acid, polycarbonate, polyolefin, polystyrene, cellulosics such as cellulose triacetate, polyphenylene sulfide, polysulfone, polyacrylates and related copolymers. It may be desirable to surface treat the substrate film in order to permit coating with aqueous or other high surface tension fluids. This may be done using one or more treatments known in the art such as subbing, corona treatment, the use of coupling agents like organotitanates, and the like. Suitably pretreated, transparent films such as subbed polyethylene terephthalate are commercially available from several sources, and are preferred.

The Registration (Concentrating or Mordanting) Layer

In the preferred three layer reflective configuration, the bottom layer of the coated stack is designed to collect and concentrate the chemical responsible for the radiant energy-detectable species, for example a dye. Effective concentration requires that this layer be highly permeable to dye, and must show some degree of thermodynamic preference for the dye over the other layers in the integral element. This dye affinity can be the result of electrostatic interactions (ionic or dipolar), covalent bonding, hydrophobicity matching, hydrogen bonding, or any other physical mechanism that encourages the accumulation of the detectable species in this layer. In the case of direct desorption of a dye from an adsorbent, the affinity of the mordanting agent must be balanced against that of the adsorbent so as to prevent spontaneous transfer of dye to the mordant in the absence of analyte.

Mordanting layers are well-known in instant photography and prior art integral analytical elements. Typically, a mordant layer consists of an ionic polymer of opposite charge to the dye to be mordanted. The dye affinity of the mordant can be controlled by altering its charge density either by copolymerization or dilution with a compatible non-mordanting polymer. Alternatively, the mordant polymer can be crosslinked to reduce its degree of swell and hence the amount of binding sites actually available for dye binding.

For anionic dyes, such as those commonly used in photographic applications, a wide range of cationic polymers, both commercial and custom-made, have been proposed. Commercial materials mentioned in prior art include the MIRAPOL line of cationic polymers (Rhodia), the CELQUAT cationic polymers (National Starch), cationic lattices such as HX42-1 (Interpolymer Corp.), hydroxypropyl trimethyl ammonium chloride hydroxyethylcellulose (POLYMER JR, Amerchol), and many others. These materials may be diluted in film forming neutral polymers such as polyvinylpyrrolidone, polyvinyl alcohol, cellulose ethers, polyvinyl butyral, polyacrylamide, or any other polymers that are compatible with the mordant and plasticizer/solvent and permeable to dye. Cationic dyes may be mordanted with anionic polymers such as carboxymethyl cellulose, polystyrenesulfonic acid salts, polyacrylic acid salts, naturally occurring anionic polymers such as alginic acid and carrageenan, copolymers of maleic acid such as those in the GANTREZ line (ISP), and many others. These may be diluted with compatible nonionic polymers such as those mentioned earlier. The polymer counterions may be varied to adjust compatibilities, regulate crosslinking, and achieve differing degrees of dye affinity.

For most purposes, it is desirable that this layer be transparent and uncolored. This is achieved by selecting components for compatibility in both the wet and dry states. This includes small molecules such as the plasticizer/solvent (s), preservatives, and surfactants. The last can be of value in insuring optimal coating quality, thereby maximizing transparency. In general, it is desirable to avoid surfactants with charge opposite to the mordanting polymer. Thus, for cationic mordants, a cationic wetting or leveling agent may be used, for example FLUORAD FC-135 (3M) or AEROSOL C-61 (Cytec). Anionic mordants can benefit from anionic wetting agents such as AEROSOL OT (Cytec) or RHODACAL DSB (Rhodia). Of course, either type of mordant could be compatible with many of the typical nonionic and amphoteric surfactants.

It is generally necessary for the mordant layer to be largely insoluble in the solvent being used to coat the next layer atop it. This may be achieved either by appropriate selection of component polymers, by design of the overcoat fluid, or by crosslinking the mordanting layer. For example, a hydrophilic mordant layer such as one composed of sodium carboxymethylcellulose would tolerate being overcoated with a reflecting layer using an organic solvent such as isopropanol or 2-butanone as its solvent. If it is desired to coat the overcoat from water, the mordant layer can have its solubility and degree of swell reduced to a usable level by adding water-insoluble binders such as polyvinylbutyral (added as e.g. an alcoholic solution), self-crosslinking binders like GOHSEFIMER Z-200 (a modified polyvinyl alcohol available from Performance Chemicals, Inc.) or X-LINK 25-2813 (a self-crosslinking vinyl acrylic latex from National Starch), or standard crosslinkers for functionalities present in one or more of the polymers in the mordant layer, for example, a titanate ester such as TYZOR LE (DuPont), if carboxylic acid units are present, or materials like 1,4-butanediol diglycidyl ether, POLYCUP 172 (Hercules), or glyoxal if hydroxyl groups are present.

The coating process is simplified if the crosslinking agents are heat activated. Then the mordant layer can be coated without concern for fluid viscosity buildup during the coating process. Crosslinking is then triggered by the drying process. Another possible implementation is to coat multiple layers at once, as is done in the photographic industry using cascade coating techniques; by suitable adjustment of coating layer densities and viscosities it is often possible to coat several water-based layers atop each other at once with minimal mixing.

Reflecting Layer

In the presently preferred embodiment of the dye desorption analytical element, the next layer to be coated is a reflecting layer. This would be a light-colored, preferably white, opaque layer imbibed with plasticizer/solvent and permeable to dye or dye precursor. Opacity and reflectance is achieved by the use of reflecting pigments such as titanium dioxide, barium sulfate, aluminum powder, zinc oxide, or other scattering particles.

Permeability is achieved by choosing polymer film formers that are well swollen by the plasticizer/solvent. For example, polyols such as glycerol are excellent plasticizers for most grades of polyvinyl alcohol, and dyes that are somewhat soluble in glycerol move easily through an appropriately formulated layer of titanium dioxide dispersed in polyvinyl alcohol.

Factors that control the effectiveness of the reflecting layer include pigment type, pigment volume concentration, pigment dispersant type and degree of dispersion, and coating thickness (coverage). It is necessary to optimize these parameters for each combination of materials making up the reflecting layer in order to get high opacity and reflectivity without impeding dye migration, layer mechanical integrity, and coating quality. The choice of opacifying pigment is a key parameter in reflecting layer formulation. Titanium dioxide is the preferred pigment because of its high reflectivity and covering power. There are many grades of titanium dioxide on the market. Of these different grades, rutile pigments are preferred to anatase titanium dioxide because of their lower photoactivity. Average primary particle size for optimum optical properties is in the range of from 0.1 to 1.0 micrometers and preferably of from 0.3 to 0.5 micrometers. It is further preferred to use a rutile pigment that is surface modified by precipitation of a shell of other oxide, typically one or more of silicon dioxide, aluminum oxide, or zirconium dioxide, over the pigment particles.

These core-shell pigments display reduced dye photodegradation and easier dispersability which are both desirable. Examples of such modified titanium dioxides can be found in most titanium dioxide pigment manufacturer's lines, as exemplified by the pigments of the TI-PURE R-900 line (DuPont), Kemira's RDD and 650, Kronos 2310, 2102 and 2160, and similar pigments.

The amount of pigment in the layer can vary over a wide range, depending on the particular pigment, how well dispersed it is, what other materials are in the pigment layer, and how thick this layer is coated. For titanium dioxide, coverages can range from 5 $g/m^2$ to 40 $g/m^2$, preferably in the range of 10 to 25 $g/m^2$. Layer thickness can be in the range of from 3 to 30 $\mu$m, preferably from 5 to about 20 $\mu$m. Pigment volume concentration can range from 25 percent to 75 percent, limited by the rheology of the coating fluid, the mechanical integrity of the dry layer, and the resistance to dye passage through this layer caused by the solid pigment particles. The required amount of titanium dioxide can be reduced be incorporation of low refractive index particles such as polytetraflouroethylene latices or ROPAQUE (Rohm & Hass) air encapsulates as is well known in the paint industry.

In order to achieve sufficient opacity to hide the detection layer from view, the pigment particles need to be thoroughly dispersed. Standard pigment dispersion methods as used in the paint industry are suitable, for example, ball milling, homogenizing, sonicating, impinging high-pressure flows, Cowles or Hockmeyer blades, and the like. It is possible to prepare the titanium dioxide as a dispersion in coating solvent, and then add the film-forming binder in a second step, as is often done for paint manufacture, or it is possible in some cases to disperse the pigment directly into a solution of the binder resin in coating solvent and plasticizer/solvent.

To produce a stable dispersion, it is desirable in most instances to use dispersant additives to insure complete dispersion and reduce flocculation and settling; this may however be unnecessary if the binder polymer has sufficient pigment dispersing properties itself, for example gelatin. Pigment dispersants can be surfactants or polymers, charged or uncharged, and may be used singly or in combination. It is necessary that the dispersants chosen be compatible with the binder and plasticizer/solvent. Otherwise the coating fluid may be unstable, or pigment flocculation and surface defects may occur during drying.

Titanium dioxide is generally dispersed in aqueous media with the aid of low molecular weight, anionic polymers such as polyacrylates like COLLOID 111 (Rhodia), polymethacrylates such as DAXAD 30 (Hampshire Chemical), naphthalenesulfonate-formaldehyde condensates such as TAMOL (Rohm & Hass), or blends with surfactants such as SURFYNOL CT-131 (Air Products). Small molecules like pyrophosphate salts and anionic surfactants such as GEROPON SS-O-75 (Rhodia) may also be suitable. It is desirable that the charge on the dispersant be the same as that of the dye or dye precursor, so as to avoid mordanting of the dye in the reflecting layer. For cationic dyes, cationic dispersants such as AEROSOL C-61 (Cytec), WITFLOW 953 (Witco), and cationic polymers like NALCO TX 7991 (Nalco Chemical) may be useful. Alternatively, nonionic dispersants such as the SOPROPHOR series (Rhodia), GLUCOPON 425N (Henkel), or GAFAC P-904 (ISP) may be tried, but they are generally somewhat less effective. Mixtures of charged and uncharged dispersants are also useful. Similar more hydrophobic dispersants of all three charge types are available for use in organic solvent-based coating fluids.

It may also be of value to use a pigment wetting or grind aid as part of the dispersion process. Representative materials include SURFYNOL 104, CT-121, and CT-136 (Air Products), WITCO 960, WITFLOW 963 (Witco), and DISPERBYK 183 (Byk). SURFYNOL CT-136 and DISPERBYK 183 can also serve as dispersants.

Any binders compatible with plasticizer/solvent, and dispersant if used, and that provide adequate dye diffusion rates are suitable. The weight ratio of pigment to binder can range of from 1:1 to 20:1, preferably in the range of from 5:1 to 9:1. The preferred ratio will depend to some degree on the choice of binder and the amount of plasticizer/solvent incorporated into it.

Other additives commonly used in the coatings, such as wetting agents, defoamers, and biocides can be incorporated into the coating. There are a wide selection of suitable materials commercially available. The primary requirement these materials must meet for use in a dye desorption analytical element is that they must either not be able to migrate to the detection layer, or should not be able to displace dye from the adsorbent. Some materials that have proven useful in systems based on activated carbon adsorbent include sodium benzoate and methanol as biocides, SURFYNOL 104PA and SURFYNOL 61 as wetting agents, and SURFYNOL DF-210 defoamer.

Detecting,Layer

Over the reflecting layer is coated the layer containing the dye desorption detection system. Exemplary adsorbents useful in the detection system include activated carbon, silica, alumina, ion exchange resins and molecular sieves. Also useful are polymers or polymer latices capable of binding dyes ion exchange resins like AMBERLITE IR 120 (Rohm & Hass) and molecular sieves such as 4A° sieves (W. R. Grace). Also useful are polymers or polymer latices capable of binding dyes. For example, polymers containing vinylprrolidone units are known to have an affinity for many classes of dyes, but as the interactions are weak, other molecules with comparable polarity and hydrogen-bonding characteristics could serve to displace these dyes and hence be detected. Particulate neutral polymeric adsorbents such as AMBERLITE XAD series (Rohm & Hass) are also applicable.

If colorless dye precursors and a white adsorbent are used, it may be possible to omit the reflecting layer. However, in most cases it will be advantageous to separate the reflection and detection functions to achieve maximum reflectivity without limiting the selection of detection materials. For example, the reflecting layers described above can be made sufficiently opaque to completely hide a layer of activated carbon and still be permeable to dyes.

Once a combination of adsorber and agent to be desorbed has been chosen, the combined material can be coated, over the reflecting layer using the same or different binders. Requirements for the binder are that the combination of binder and coating fluid not desorb the indicating species and that the binder must not block release of the indicating species, either directly or due to insufficient permeability to the analytes of interest.

Finding appropriate binders is a process that is sensitive to the choice of plasticizer/solvent as well as adsorbent and dye or dye precursor. For example, although in an analytical element for the detection of aromatic hydrocarbons by desorption of Methylene Blue from activated carbon using a diol plasticizer/solvent, polyvinyl alcohol is a satisfactory binder for a titanium dioxide reflective layer, but not for the activated carbon detecting layer. However, cellulosic polymers such as KLUCEL (Hercules) or METHOCEL (Dow) do permit dye to leave the carbon surface and migrate to the mordant layer. Similarly, wetting agents and other coating aids must be selected carefully to avoid interference with the detection system. Combinations of polymers may be particularly useful in this layer to maximize permeability to both analytes and dyes while providing the mechanical robustness necessary for an unprotected top layer.

The following examples are presented to illustrate the advantages of the present invention and to assist one of ordinary skill in making and using the same. These examples are not intended in any way otherwise to limit the scope of the disclosure.

EXAMPLE 1

A vapor detection system based on dye desorption was prepared as follows: a mordant layer comprising the commercially available polymer GANTREZ AN-169 (ISP) at 1300 mg/m$^2$, 2-methyl-1,3-propanediol at 7786 mg/m$^2$, and RHODACAL DSB (Rhodia) at 13.0 mg/m$^2$ was coated from water using a wound-wire rod onto a transparent, subbed polyester support from water and dried 5 minutes at 115° C. Over this layer was coated a reflecting layer containing the following materials:

| MATERIAL | COVERAGE (mg/m$^2$) |
|---|---|
| TI-PURE R-900 titanium dioxide (DuPont) | 26,087 |
| dispersant DAXAD 30 (Hampshire Chemical) | 137 |
| wetting agent SURFYNOL 104PA (Air Products) | 1565 |
| defoamer SURFYNOL DF-210 (Air Products) | 1159 |
| 2-methyl-1,3-propanediol (Arco Chemical) | 579 |
| AIRVOL 107 (Air Products) | 2673 |
| ammonium titanium lactate (50% solution) (Aldrich) | 406 |

These materials were coated from an aqueous dispersion that was prepared using a rotor-stator homogenizer. The coating fluid was applied using a wound-wire rod. The resultant two-layer structure was oven-dried for 20 minutes at 115° C. The magenta dye Pyronin Y (Aldrich) was adsorbed from water onto DARCO G-60 activated carbon (NORIT) at 60 mg/g carbon. The dye loaded carbon was then used to prepare a sensing layer composed as follows:

| MATERIAL | COVERAGE (mg/m$^2$) |
|---|---|
| Pyronin Y on carbon | 4930 |
| 2-methyl-1,3-propanediol | 9076 |
| METHOCEL K35LV hydroxypropylmethylcellulose (Dow) | 148 |
| polyethylene oxide 600K (Aldrich) | 58.3 |
| WITCOBOND W-213 polyurethane latex (Ashland Chemical) | 430 |

This layer was coated from water with a wire-wound rod, and air-dried. The completed detector was tested by attaching it to a clear glass plate that was then glued with POLECTRON 430 adhesive latex (ISP) onto a jar containing a small beaker of test solvent that served as a source of vapors to be detected.

This detector, prior to exposure, had an optical reflection density (OD) in the magenta (CIE status A) of 0.22 and a white visual appearance. After 160 min. of exposure to dichloromethane vapors, the viewing side of the detector became deep magenta with a magenta reflection density of 0.84. When exposed to toluene vapors at ambient temperature for 8 hours, the detector displayed a reflection density of 1.44.

EXAMPLE 2

Different mordant layers were prepared from GANTREZ AN-169 in a manner analogous to Example 1, except that the amount and type of base was varied. Bases used included sodium and potassium hydroxides and lithium carbonate, as well as amines including ethanolamine, diethanolamine, and triethanolamine (all from Aldrich). These mordants were used to prepare multi-layer structures comparable to Example 1. All gave significant color on exposure to toluene vapors. Maximum optical densities were as follows:

| BASE | DYE | % NEUTRALIZATION | MAGENTA Dmax (Dmin) |
|---|---|---|---|
| ethanolamine | Pyronin Y | 100 | 1.43 (0.20) |
| diethanolamine | " | 100 | 1.56 (0.20) |
| triethanolamine | " | 100 | 1.45 (0.19) |
| triethanolamine* | " | 100 | 1.15 (0.19) |
| triethanolamine | " | 33 | 1.71 (0.19) |
| NaOH | " | 33 | 1.71 (0.20) |
| Li2CO3 | " | 33 | 1.76 (0.19) |
| no base | " | 0 | 1.72 (0.22) |
| NaOH | Methylene Blue (Aldrich) | 33 | 2.06 (0.19) |
| KOH | Methylene Blue (Aldrich) | 33 | 1.39 (0.19) |
| NaOH | Thionin perchlorate | 33 | 1.45 (0.22) |

-continued

| BASE | DYE | % NEUTRALIZATION | MAGENTA Dmax (Dmin) |
|---|---|---|---|
| no base | (Aldrich) Thionin perchlorate (Aldrich) | 0 | 2.12 (0.21) |

*GANTREZ ES-225 in place of GANTREZ AN-169

EXAMPLE 3

Various loadings of Pyronin Y on carbon were prepared and incorporated into the top layer of a multi-layer coating similar to Example 1. Pieces of these coatings were exposed to vapors of various solvents until the color on the mordant side did not increase further. The results are reported in units of percentage reflectance as measured on a home-built spectrophotometer.

| LOADING (mg dye/g carbon) | TOLUENE | CH2Cl2 | AMYL ACETATE |
|---|---|---|---|
| 19 | 2 | ~0 | ~0 |
| 40 | 5 | 2.5 | ~1 |
| 60 | 10 | 7.5 | 3 |
| 80 | 11 | 10.5 | 4.5 |

EXAMPLE 4

An alternative mordant layer was formulated as follows:

| MATERIAL | COVERAGE (mg/m$^2$) |
|---|---|
| VERSA TL-502 polystyrenesulfonate (Alco Chemical) | 460.7 |
| GOHESFIMER Z-200 (Performance Chemicals) | 26.50 |
| AIRVOL 125 (Air Products) | 1677.0 |
| polyvinylpyrrolidone K-15 (ISP) | 462.4 |
| 1,2-propanediol (Aldrich) | 21269.0 |
| NaOH | 3.40 |
| RHODACAL DSB surfactant | 105.1 |

EXAMPLE 5

An alternative carbon layer was formulated as follows:

| MATERIAL | COVERAGE (mg/m$^2$) |
|---|---|
| Pyronin Y on carbon | 5151.5 |
| 2-methyl-1,3-propanediol | 9485.0 |
| METHOCEL K35LV hydroxypropylmethylcellulose | 154.3 |
| polyethylene oxide 600K | 60.9 |
| DUR-O-SET SB-321 polyvinyl acetate latex (National Starch) | 258.6 |

EXAMPLE 6

The maximum viewing surface dye densities resulting from exposure to various vapors of the coated structure of Example 1 were determined by reflection densitometry using an X-RITE 310 densitometer (X-Rite Systems, Grandville, Mich.) in Status A mode. Two coatings were compared, that of Example 1 and another identical except for the replacement of Pyronin Y by the blue-violet dye Thionin perchlorate.

| | Pyronin Y 60 mg/g on Darco G-60 | Thionin C104 120 mg/g on Darco G-60 |
|---|---|---|
| toluene | 0.71/0.30/1.72/0.99 | 1.69/1.09/2.11/0.63 |
| CH2Cl2 | 0.56/0.41/1.03/0.62 | 1.59/1.15/1.76/0.72 |
| amyl acetate | 0.49/0.27/1.01/0.52 | 0.57/0.47/0.53/0.37 |
| i-octane | 0.18/0.18/0.23/0.21 | 0.25/0.24/0.25/0.24 |

Dye densities are in units of reflectance optical density in the order visual/cyan/magenta/yellow. Unexposed material has $D_{min}$ = 0.18/0.19/0.22/0.21.

EXAMPLE 7

Various liquids were applied to Example 1 coatings using a wire-wound rod to apply a 15 μm thick coating over the carbon layer. The untreated coatings had a $D_{min}$ of 0.21/0.22/0.24/0.23:

| LIQUIDS | $D_{max}$ after 4 hours |
|---|---|
| (solutions in 2-methyl-1,3-propanediol) diesel fuel, 5% | 0.22/0.21/0.33/0.28 |
| 1,10-phenanthroline (Alfa) (5%) | 0.65/0.36/1.41/0.49 |
| pyrene (Aldrich) (saturated) | 0.44/0.45/0.46/0.45 |
| tris-2-pyridyl-1,3,5-triazine (Aldrich) (saturated) | 0.50/0.34/0.82/0.44 after 6 hours |

EXAMPLE 8

The effect of toluene vapor on three devices identical except for containing three different dyes was examined. The dye loadings were chosen to give comparable $D_{min}$ values:

| Dye | Dmin | Dmax |
|---|---|---|
| Pyronin Y | 0.10/0.09/0.10/0.11 | 1.19/0.58/2.63/1.97 |
| Methylene Blue | 0.11/0.11/0.11/0.12 | 1.82/1.32/2.06/1.27 |
| Thionin perchlorate | 0.15/0.12/0.12/0.12 | 2.49/1.98/2.64/1.29 |

EXAMPLE 9

Various coated layer structures were prepared using either 1,2-propanediol (Aldrich) or 1,4-butanediol (Arco) in place of 2-methyl-1,3-propanediol. These coatings all behaved similarly, but the 1,2-propanediol gave a somewhat lower $D_{min}$ than the other two, and coating behaviors were less reproducible with it, presumably as a result of evaporation loss of the 1,2-propanediol during oven drying. With certain dye and vapor combinations, 1,4-butanediol gave a slightly higher $D_{min}$ than did 2-methyl-1,3-propanediol. Dipropylene glycol (Aldrich) did not give satisfactory coatings with this system.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A broad screen analytical detection element, capable of detection of several classes of gas or liquid analytes, said detection element comprising
    a first region comprising a solid and adsorbed said solid a radiant energy-detectable material or a material capable of producing a radiant energy-detectable material, wherein said radiant energy-detectable material or said material capable of producing a radiant energy-detectable material is desorbable by a target analyte; and
    a second region for sequestering radiant energy-detectable material
    (a) desorbed from or
    (b) produced by material desorbed from said solid prior to detection of said radiant energy-detectable material,
    wherein either said first region or said second region further comprises a high boiling plasticizer/solvent and wherein classes of gas or liquid analytes are detected.

2. The analytical detection element of claim 1 wherein said solid is selected from the group consisting of activated carbon, silica, alumina, ion exchange resin, molecular sieve and particulate organic polymeric adsorbent.

3. The analytical detection element of claim 1 wherein said detection element is multi-layered and said first region and said second region are in separate layers in said detection element.

4. The analytical detection element of claim 1 wherein said detection element is in multiple small pieces.

5. The analytical detection element of claim 1 further comprising a background region against which radiant energy-detectable material can be detected.

6. The analytical detection element of claim 1 wherein a material capable of producing a radiant energy-detectable material is adsorbed on said solid and said material capable of producing a radiant energy-detectable material is capable of initiating a chemical reaction or physical process that results in a change in a radiant energy-detectable material residing in said second region.

7. The broad screen analytical detection element of claim 1, wherein said first region constitutes a sample capture layer, said second region contains (a) a concentrating or mordanting layer, (b) an opacifying or reflecting layer or (c) both said layers; and wherein said analytical detection element also comprises a transparent base layer.

8. The analytical detection element of claim 7, wherein said second region is between said first region and said transparent base layer in said detection element.

9. The analytical detection element of claim 8, wherein said detection element contains one or more additional layers.

10. A broad screen analyte detection badge comprising the analytical detection element of claim 1, wherein classes of gas or liquid analytes are detected.

11. A broad screen analyte detection badge comprising the broad screen analytical detection element of claim 7, wherein classes of gas or liquid analytes are detected.

12. A coating material comprising the broad screen analytical detection element of claim 1, wherein classes of gas or liquid analytes are detected.

13. A broad screen analytical detection element, capable of detection of several classes of gas or liquid analytes, said detection element comprising
    a first region comprising a solid and adsorbed on said solid a radiant energy-detectable material or a material capable of producing a radiant energy-detectable material, wherein said radiant energy-detectable material or said material capable of producing a radiant energy-detectable material is desorbable by a target analyte; and
    a second region for sequestering radiant energy-detectable material desorbed from or produced by material desorbed from said solid prior to detection of said radiant energy-detectable material,
    wherein said detection element is in the form of multiple small pieces and
    wherein classes of gas or liquid analytes are detected.

14. A broad screen method for detection of one or more analytes or classes of analytes, said method comprising the steps of:
    providing an analytical detection element, said detection element comprising a solid and adsorbed on said solid a radiant energy-detectable material or a material capable of producing a radiant energy-detectable material, wherein said radiant energy-detectable material or said material capable of producing a radiant energy-detectable material is desorbable by a target analyte;
    exposing said analytical detection element to a population of molecules possibly containing said target analytes for a period of time sufficient to permit desorption by said target analytes of said radiant energy-detectable material or said material capable of producing a radiant energy-detectable material from said solid, wherein said radiant energy-detectable material or said material capable of producing a radiant energy-detectable material desorbed by said target analyte is made mobile by the presence of a high boiling plasticizer/solvent;
    determining the amount of said radiant energy-detectable material or said material capable of producing a radiant energy-detectable material desorbed from said solid; and
    correlating the amount of said radiant energy-detectable material or said material capable of producing a radiant energy-detectable material desorbed from said solid with the amount of target analyte present in said population of molecules.

15. The method of claim 14 wherein, in said providing step, said solid in said analytical detection element is selected from the group consisting of activated carbon, silica, alumina, ion exchange resin and molecular sieve.

16. The method of claim 14 wherein, in said providing step, said analytical detection element is multi-layered and said first region and said second region are in separate layers in said detection element.

17. The method of claim 14 wherein, in said providing step, said analytical detection element further comprises a background region against which radiant energy-detectable material can be detected.

18. The method of claim 14 wherein, in said analytical detection element in said providing step, a material capable of producing a radiant energy-detectable material is adsorbed on said solid and said material capable of producing a radiant energy-detectable material is capable of initiating a chemical reaction or physical process that results in a change in a radiant energy-detectable material residing in said second region.

19. The method of claim 14 wherein said high boiling plasticizer/solvent is selected from the group consisting of alcohols, diols and higher polyols, sulfoxides, amides, esters, carbonates and ketones.

20. A broad screen analytical detection element, capable of detection of several classes of gas or liquid analytes, said detection element comprising a first region comprising (a) a solid and adsorbed on said solid a radiant energy-detectable material or a material capable of producing a radiant energy-detectable material, wherein said radiant energy-detectable material or said material capable of producing a radiant energy-detectable material is desorbable by a target analyte, and (b) a high boiling plasticizer/solvent, wherein several classes of gas or liquid analytes are detected.

21. The analytical detection element of claim 20 wherein said first region is applied to a surface as a coating material.

correlating the amount of said radiant energy-detectable material or said material capable of producing a radiant energy-detectable material desorbed from said molecularly permeable solid with the amount of target analyte present in said population of molecules, wherein one or more analytes or classes of analytes are detected.

22. The method of claim 19 wherein said high boiling plasticizer/solvent is selected from the group consisting of propylene carbonate; 1,4-butanediol; 1,2-propanediol, and 2-methyl-1,3-propanediol.

* * * * *

UNITED STATES PATENT AND TRADEMARK OFFICE
CERTIFICATE OF CORRECTION

PATENT NO. : 6,812,035 B1
APPLICATION NO. : 09/350466
DATED : November 2, 2004
INVENTOR(S) : Mark T. Spitler et al.

It is certified that error appears in the above-identified patent and that said Letters Patent is hereby corrected as shown below:

Column 1, line 50, "Streptococcus" should be italicized and read --*Streptococcus*--;

Column 1, line 68, "calorimetrically" should read --colorimetrically--;

Column 2, line 12, "Ca++" should read --$Ca^{++}$--;

Column 3, line 47, delete the word "us";

Column 8, line 35, "De" should read --be--;

Column 16, line 64, "$D_{min}$" should read --$D_{max}$--;

Column 16, line 68, "$D_{min}$" should read --$D_{max}$--;

Column 17, claim 1, line 13, "said solid" should read --on said solid--;

Column 18, claim 14, line 47, after "population of molecules" please insert the following:

--correlating the amount of said radiant energy-detectable material or said material capable of producing a radiant energy-detectable material desorbed from said molecularly permeable solid with the amount of target analyte present in said population of molecules,
wherein one or more analytes or classes of analytes are detected--; and

UNITED STATES PATENT AND TRADEMARK OFFICE
CERTIFICATE OF CORRECTION

PATENT NO.       : 6,812,035 B1
APPLICATION NO.  : 09/350466
DATED            : November 2, 2004
INVENTOR(S)      : Mark T. Spitler et al.

It is certified that error appears in the above-identified patent and that said Letters Patent is hereby corrected as shown below:

Column 20, after claim 21, lines 3-9 should be deleted.

Signed and Sealed this

Twentieth Day of May, 2008

JON W. DUDAS
*Director of the United States Patent and Trademark Office*